United States Patent
Huey et al.

(10) Patent No.: US 11,294,404 B1
(45) Date of Patent: Apr. 5, 2022

(54) AIR-OXYGEN BLENDER WITH PERIODIC PRESSURE VENTING

(71) Applicant: Bio-Med Devices, Inc., Guilford, CT (US)

(72) Inventors: Raymond J. Huey, Orange, CT (US); Jack N. Sandgren, Guilford, CT (US); Shamili Krishnamurthy, Branford, CT (US); Ronald C. Baktis, Wallingford, CT (US)

(73) Assignee: Bio-Med Devices, Inc., Guilford, CT (US)

( * ) Notice: Subject to any disclaimer, the term of this patent is extended or adjusted under 35 U.S.C. 154(b) by 0 days.

(21) Appl. No.: 17/032,857

(22) Filed: Sep. 25, 2020

(51) Int. Cl.
*A61M 16/00* (2006.01)
*G05D 11/13* (2006.01)
*F16K 15/14* (2006.01)
*A61M 16/12* (2006.01)
*G01N 33/00* (2006.01)
*A61M 16/10* (2006.01)

(52) U.S. Cl.
CPC ......... G05D 11/138 (2013.01); A61M 16/122 (2014.02); F16K 15/147 (2013.01); G01N 33/0073 (2013.01); *A61M 2016/1025* (2013.01); *A61M 2202/0208* (2013.01)

(58) Field of Classification Search
CPC .... G05D 11/138; G05D 11/132; G05D 11/02; G01N 33/0073; B01F 3/028; A61M 16/12; A61M 16/104; A61M 16/20; A61M 16/203; A61M 16/122; A61M 16/207
See application file for complete search history.

(56) References Cited

U.S. PATENT DOCUMENTS

| | | | |
|---|---|---|---|
| 3,727,627 A | 4/1973 | Bird et al. | |
| 4,020,834 A | 5/1977 | Bird | |
| 4,127,123 A | 11/1978 | Bird | |
| 4,141,354 A | 2/1979 | Ismach | |
| 4,592,349 A | 6/1986 | Bird | |
| 4,702,240 A | 10/1987 | Chaoui | |

(Continued)

OTHER PUBLICATIONS

Bio-Med Devices; Air/Oxygen Blender Service Manual; Revised Apr. 22, 2015.

(Continued)

*Primary Examiner* — Margaret M Luarca
(74) *Attorney, Agent, or Firm* — St Onge Steward Johnston and Reens LLC

(57) ABSTRACT

An air/oxygen blender, optionally with an associated oxygen analyzer, is provided with an exhaust valve in fluid communication with one or more of a proportioning valve and a gas outlet which periodically opens to vent gas therefrom. The exhaust valve is preferably an electrically actuated valve, most preferably a solenoid valve, controlled by a control unit which periodically opens the exhaust valve. In another embodiment, an oxygen analyzer is provided with an exhaust valve in fluid communication with an oxygen sensing chamber. Preferably, the control unit controls the frequency of exhaust valve opening and the time period of exhaust valve opening. A method of prevention of contamination of a lower pressure source air or source oxygen connected to an air/oxygen blender is accomplished by periodically venting of gas from the exhaust valve.

21 Claims, 13 Drawing Sheets

(56) References Cited

U.S. PATENT DOCUMENTS

| | | | |
|---|---|---|---|
| 5,000,173 A | | 3/1991 | Zalkin et al. |
| 5,007,420 A | | 4/1991 | Bird |
| 5,074,299 A | | 12/1991 | Dietz |
| 5,116,088 A | | 5/1992 | Bird |
| 5,165,398 A | | 11/1992 | Bird |
| 5,862,802 A | | 1/1999 | Bird |
| 5,887,611 A | | 3/1999 | Lampotang et al. |
| 5,915,834 A | * | 6/1999 | McCulloh ............. A61M 16/12 366/151.1 |
| 8,006,692 B2 | | 8/2011 | Smith et al. |
| 8,402,967 B2 | | 3/2013 | Smith et al. |
| 10,543,327 B2 | | 1/2020 | Jafari et al. |
| 2007/0125374 A1 | * | 6/2007 | Smith ................. A61M 16/204 128/203.12 |
| 2011/0132366 A1 | * | 6/2011 | Ogilvie ............. A61M 16/0057 128/204.22 |
| 2014/0254305 A1 | * | 9/2014 | Caso .................. A61M 16/024 366/152.1 |
| 2017/0246419 A1 | | 8/2017 | Callaghan et al. |
| 2019/0275273 A1 | | 9/2019 | Chang |

OTHER PUBLICATIONS

Air/Oxygen Blender Instruction Manual; Revised Apr. 17, 2017.
Maxtec, MaxBlend 2, Operating Manual and Instructions for Use; Oct. 5, 2016.

* cited by examiner

AIR-OXYGEN BLENDER WITH PERIODIC PRESSURE VENTING

FIELD OF THE INVENTION

The present invention relates to the field of medical devices, particularly, air/oxygen blenders which provide oxygen-enriched air to patients.

BACKGROUND OF THE INVENTION

Acute hypoxemic respiratory failure is a common reason for hospitalization and may be caused by disease or injury. Hypercapnic respiratory failure will also typically require hospitalization. Oxygen supplementation is an important aspect of supportive care for such conditions. In a typical hospital environment, respiratory support may range from a low-flow oxygen-enriched air or oxygen delivered via nasal cannula or mask, to a high-flow oxygen-enriched air delivered at a volume and rate which equals or exceeds the patient's inspiratory flow demand via nasal cannula, various masks including mask CPAP and resuscitation bags, or via intubation.

Air/oxygen blenders may be used in both low-flow and high-flow patient respiratory support. A typical air/oxygen blender will allow mixing of air and oxygen to provide patient ventilation air ranging from 21%-100% oxygen (0.21 to 1.0 $FiO_2$) at gas flow rates up to 60 L/min. An air/oxygen blender can provide precise oxygen delivery independent of the patient's inspiratory flow demands, and can provide a positive end-expiratory pressure (PEEP).

An air/oxygen blender may be used either without, or with, a mechanical ventilator. A mechanical ventilator is typically used for high-flow respiratory support and will typically cycle between an inspiration stage that uses positive pressure to move air into the lungs of a patient, and an expiration stage during which the positive pressure is released and the patient will exhale passively due to the lungs' elasticity. Mechanical ventilator control systems may trigger an inspiration cycle when the patient takes a breath, and provide support for the patient's breathing cycle, or the inspiration and expiration cycle may be completely under the control of the ventilator.

A standard medical air/oxygen blender is the Bird air/oxygen blender, which operates generally according to the design principles disclosed by Bird in U.S. Pat. No. 3,727,627, the disclosure of which is hereby incorporated by reference. A typical air/oxygen blender has a housing having air supply inlet and oxygen supply inlet D.I.S.S. fittings located on the bottom face of the housing. Source air and oxygen are typically supplied at a pressure of 50 psi (345 kPa) to these inlets. Each inlet fitting contains a duckbill check valve positioned with its valve bill pointing upwards and inwards into the blender housing to prevent possible reverse gas flow from the blender into the air or oxygen supply. Although it is conceptually possible to use other types of check valves in the gas inlets, duckbill valves have significant advantages over ball check valves in an air/oxygen blender. In particular, duckbill valves will open for even a very low pressure and flow, thus providing immediate free gas flow even at low flow rates. Additionally, duckbill valves provide a very high flow rate if needed. Air/oxygen blenders are used for many different types of patients, from neonatal to pediatric to adult. It is to be appreciated that the gas flow rates required by neonatal patients is substantially less than that required by adults, and thus the duckbill valve's ability to open and provide a steady, constant gas flow even for very low flow rates is very beneficial to patient care. In contrast, other types of check valves may not provide acceptable functionality over the full range of flow rates. For example, a spring loaded ball check valve requiring a higher opening pressure may cycle open and closed at a low neonatal flow rate, delivering gas in pulses, which can lead to inconsistent $O_2$ concentration in the air supplied to the patient. However, specifying a spring loaded ball check valve which opens at a lower opening pressure has the potential problem that it will not close when a gas is supplied at a higher pressure than the other gas, compromising the effectiveness of the pressure balancing stages discussed below.

FIG. 1 is a schematic illustration of an air/oxygen blender which has two pressure balancing stages and a proportioning stage. The pressure balancing stages equalize the operating pressure of the air and oxygen. The gas sources enter the lower section of the blender where they pass by a shuttle spool. This spool floats in the reed alarm cross channel and remains generally centered provided the air and oxygen pressures remain within a certain psi range of each other (typically 20 psi or 30 psi), thus blocking passage of gas to the reed alarm in the reed alarm vertical channel. The gases continue into the first balancing stage.

The first balancing stage comprises a cavity divided by a resilient diaphragm. The diaphragm divides the cavity into two chambers, an air chamber and an oxygen chamber. A valve spool extends through and is bonded to the diaphragm. Each end of the valve spool has a valve closing structure which may for example be a ball or a disk or a frustoconical element. Each of the air chamber and oxygen chamber have an opening and/or passageway through which the valve spool extends, and has a valve seat against which the valve closing structure seats to close the opening and/or passageway.

Air and oxygen enter into the air chamber and the oxygen chamber on opposite sides of the cavity. If the air and oxygen pressures are equal the diaphragm does not move and the air and oxygen will flow at the delivered pressure. If one gas is at a higher pressure, the diaphragm will move towards the lower pressure chamber, simultaneously moving the valve closing structure on the valve spool towards the valve seat in the higher pressure chamber, and moving the valve closing structure on the valve spool away from the valve seat in the lower pressure chamber, roughly equalizing the pressure in the air and oxygen chambers.

The gases continue to a second pressure balancing stage which is the same as the first stage, in which a diaphragm responds to any difference in source pressures and equalizes these pressures by the activating the valve spool to adjust air and oxygen pressures in the air and oxygen chambers.

After the pressure balancing stages, the gases continue to a proportioning stage and are mixed to the percentage dialed in on the front panel knob. The proportioning stage has a double-ended valve with valve seats on either end. One valve seat controls the passage of air and the other valve seat controls the passage of oxygen. The front panel knob is used to set the specific $FiO_2$ blend. The knob settings range from 21% oxygen to 100% oxygen. With the front panel knob at the full counterclockwise position (21%), the double ended valve will completely close off the flow of oxygen, allowing only air to flow. By adjusting the knob to the full clockwise position (100%), the flow of air is blocked, permitting only the flow of oxygen.

The blended air/oxygen delivered from the double ended valve is delivered to the gas outlet(s). There are typically a primary outlet, and a low flow auxiliary outlet; and in some cases a third low flow outlet. Each outlet has a check valve that prevents gas from passing through it unless a hose or other device is threaded onto it. Each outlet desirably has an on/off valve to control release of gas from the blender. The primary outlet will typically be located on one side of the housing so a flowmeter may be conveniently mounted thereto and used to open/close the outlet on/off valve.

FIG. 2 illustrates delivery of an air/oxygen blend via the low-flow auxiliary outlet. The low-flow auxiliary outlet typically is provided with a bleed port. The bleed port is controlled by a valve operated by a bleed knob that opens the valve. A bleed is typically needed to obtain low flow rates with accurate $O_2$ concentration. It is commonly observed that an outlet without a bleed port, at flows less than 3 liters per minute, will deliver a gas with an oxygen concentration that does not match the setting on the front panel knob. This is due to variations caused by variations in input gas pressures, and how this interacts with the requested flow rate and the concentration setting. Thus, in typical air/oxygen blenders, the bleed port is used to bleed the gas mixture to the atmosphere when using the blender at flows of less than 15 liters/minute in a high flow blender, or less than 6 liters/minute in a medium flow blender, or less than 3 liters/minute in a low flow blender. Thus, in low flow applications such as neonatal patient applications, it is typical that the low flow outlet is used with a bleed port.

Referring now to FIG. 3, a reed alarm is located on the bottom of the housing that is activated when the difference in pressure between the two inlet gasses exceeds a selected psi difference. Typically the selected psi difference will be 20 psi or 30 psi. When the two source gases are near equal in pressure, the alarm bypass poppet valve is positioned over the bypass channel, blocking the flow of both gases. The poppet valve will remain seated until the selected psi difference occurs. Once a psi difference exceeding the selected limit is applied to the poppet, the higher gas pressure will overcome the spring force and pressure will overcome the spring force and pressure at its opposite end, thus creating a path for gas (air or oxygen) to flow into the alarm channel. The gas with the higher pressure will also flow directly to the blender outlet port and bypass the pressure balancing and proportioning stages, so that the oxygen concentration at the blender outlet will be that of the gas at the higher pressure. The blender will therefore deliver oxygen (100%) or air (21%) (whichever is at the higher pressure) until the bypass mechanism is reset.

In some instances it has been considered desirable to provide an oxygen measurement system together with the air/oxygen blender to provide a positive confirmation of the $O_2$ concentration of the gas delivered from the primary and/or auxiliary outlets. To that end, an electronic oxygen sensor is provided in fluid communication with the gas outlet as described in U.S. Pat. No. 5,887,611, the disclosure of which is hereby incorporated by reference.

A commercially available oxygen measurement system adapted to be used with standard air/oxygen blenders is the MaxO2 ME oxygen sensor and display which can be mounted to an air/oxygen blender using the MaxO2 ME Blender Kit, both available from Maxtec, LLC, Salt Lake City Utah. In some embodiments, a manifold may be attached to an auxiliary gas outlet and a gas stream extracted via the manifold and continuously measured by the oxygen measurement system.

A commercially available combination of an oxygen measurement system and standard air/oxygen blenders is the MaxBlend2, also available from Maxtec, LLC, Salt Lake City Utah.

It has been reported that hospitals and other medical facilities have sometimes encountered unexpected oxygen concentrations in patient respiratory support systems associated with air/oxygen blenders. In some cases, patient oxygen saturation has been lower than should have been obtained from the setting of the air/oxygen blender. In some cases, patient oxygen saturation has been higher than should have been obtained from the setting of the air/oxygen blender. In some cases the oxygen content of source air has been found to be significantly higher than 21%. In some cases the oxygen content of the source oxygen may be less than 100%.

It is common in many hospitals and other medical facilities to maintain an air/oxygen blender on standby for immediate use in an emergency. The air/oxygen blender is connected to the source air and oxygen. Flowmeters may be attached to one or both of the primary and auxiliary outlets. The above noted problems appear to be almost exclusively in the context of facilities which have a patient respiratory support air supply available for immediate use, particularly in neonatal facilities. The problems are resolved when the air/oxygen blender is not kept connected to the source air and source oxygen, and flowmeters and patient circuits are also not kept connected to the primary or auxiliary outlets.

It is typical that source air and source oxygen are delivered at somewhat different pressures. It is rare that they both reach the air/oxygen blender at the exact same pressure. It seems likely that the observed problems arise due to problems arising from these pressure variances, specifically, it seems likely that if the front panel knob is set at some intermediate position between 21% and 100% oxygen, that the higher pressure gas will pass through the double-ended proportioning valve and into the lower pressure gas line back to the duckbill valve at the inlet. While the duckbill valve will prevent significant backflow, it may still permit some reverse flow seepage through the valve lips. If this happens, it will cause a reverse gas flow from the blender into the lower pressure gas line. Over time, the slow, continuous reverse gas flow would contaminate a lower pressure source air with higher pressure oxygen, or a lower pressure source oxygen with higher pressure source air.

Thus, a higher pressure source oxygen line can cause the source air to have O2 levels that are higher than 21%. Alternatively, a higher pressure source air line can cause the source oxygen to have $O_2$ levels that are lower than 100%. This in turn means that the air oxygen blender would not be able to accurately deliver the dialed-in $FiO_2$ to the patient, potentially compromising the course of medical treatment. Depending on the supply gas pressures and length of time the air/oxygen blender is attached to the supply lines, and the internal valving of the source air and source oxygen systems, the contamination may be localized to one area or it can extend throughout larger sections, and potentially even the entire facility.

Accordingly, there is a need for an air/oxygen blender which solves the problems of contamination or dilution of lower pressure source air or oxygen connected to an air/oxygen blender.

SUMMARY OF THE INVENTION

The present invention relates to a solution to the problems of contamination or dilution of lower pressure source air or oxygen connected to an air/oxygen blender.

In one embodiment of the invention, an air/oxygen blender comprises a housing having a first gas inlet, a second gas inlet, a proportioning valve, and a gas outlet. The first gas inlet is in fluid communication with a first gas chamber. The second gas inlet is in fluid communication with a second gas chamber. The first and second gas inlets have check valves located between their respective inlets and chambers. In one embodiment, the check valves are duckbill valves. The proportioning valve is in fluid communication with the first gas chamber, and the second gas chamber, and the gas outlet. In one embodiment, the proportioning valve is a double-ended valve with valve seats on either end operable by reciprocating motion to close or open ends of the additional gas channels to thereby release either the first gas or the second gas or a mixture thereof.

An exhaust valve is in fluid communication with the proportioning valve and the gas outlet and periodically opens to vent gas therefrom. Preferably, the exhaust valve is an electrically actuated valve, most preferably a solenoid valve, controlled by a control unit which periodically opens the exhaust valve. Preferably, the control unit controls the frequency of exhaust valve opening and the time period of exhaust valve opening.

In one embodiment, the air/oxygen blender is provided with an associated oxygen analyzer. The oxygen analyzer has an oxygen sensor located in a sensing chamber and a display for display of a gas oxygen percentage. In one such embodiment, the proportioning valve and gas outlet are in fluid communication with the sensing chamber containing an oxygen sensor, and the exhaust valve is in fluid communication with the sensing chamber, and vents gases from the sensing chamber.

In another embodiment, an oxygen analyzer is provided with an exhaust valve in fluid communication with an oxygen sensing chamber.

A method of prevention of contamination of a lower pressure source air or source oxygen connected to an air/oxygen blender, where the air/oxygen blender has a housing having a first gas inlet, a second gas inlet, a proportioning valve, and a gas outlet; and an exhaust valve, in fluid communication with the proportioning valve and the gas outlet, comprises periodically opening the exhaust valve to vent gas therefrom. In one embodiment, the exhaust valve is an electrically actuated exhaust valve, preferably a solenoid valve, controlled by a control unit which periodically opens the exhaust valve to vent gas therefrom.

Additional features and details of embodiments of the invention will now be described in reference to the drawings.

DETAILED DESCRIPTION OF THE INVENTION

Figure 1:
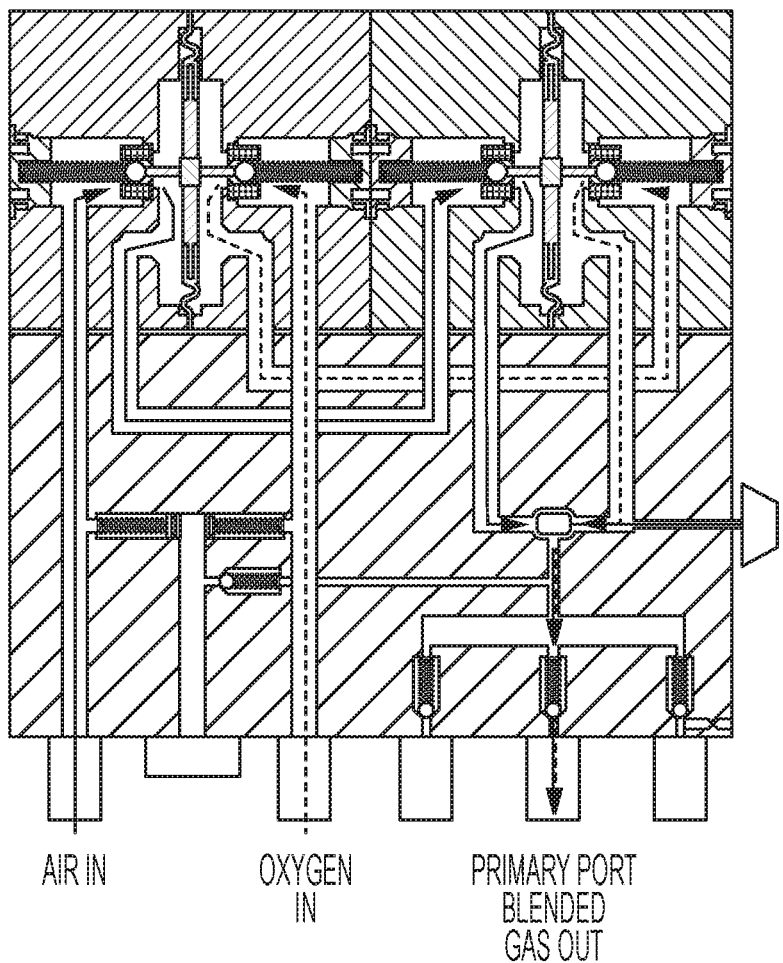
FIG. 1 is a schematic illustration of a prior art air/oxygen blender, with blended gas dispensed via a primary gas outlet.
Figure 2:
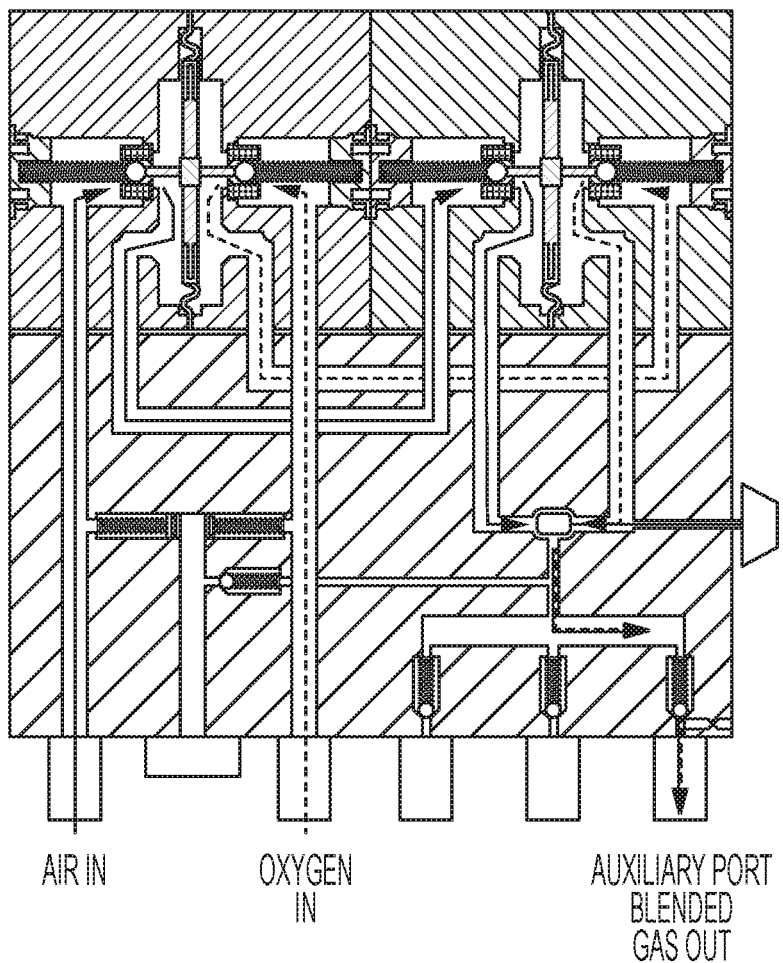
FIG. 2 is a schematic illustration of a prior art air/oxygen blender, with blended gas dispensed via an auxiliary gas outlet.
Figure 3:
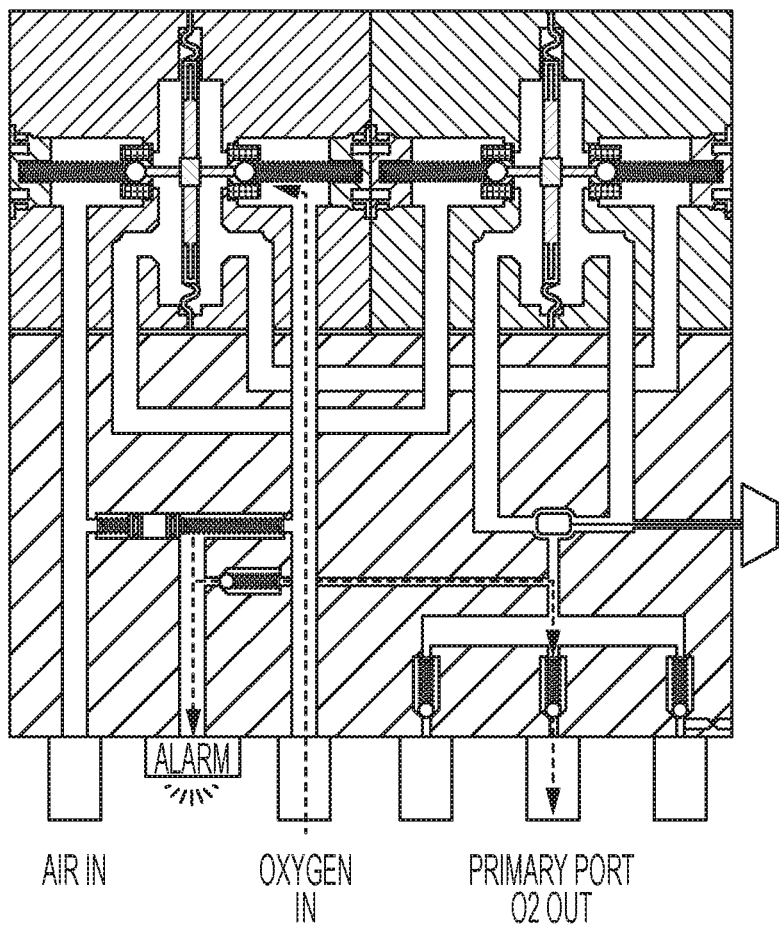
FIG. 3 is a schematic illustration of a prior art air/oxygen blender, showing an alarm condition arising when the air and oxygen source pressures exceed the selected setpoint for activating the alarm.
Figure 4:
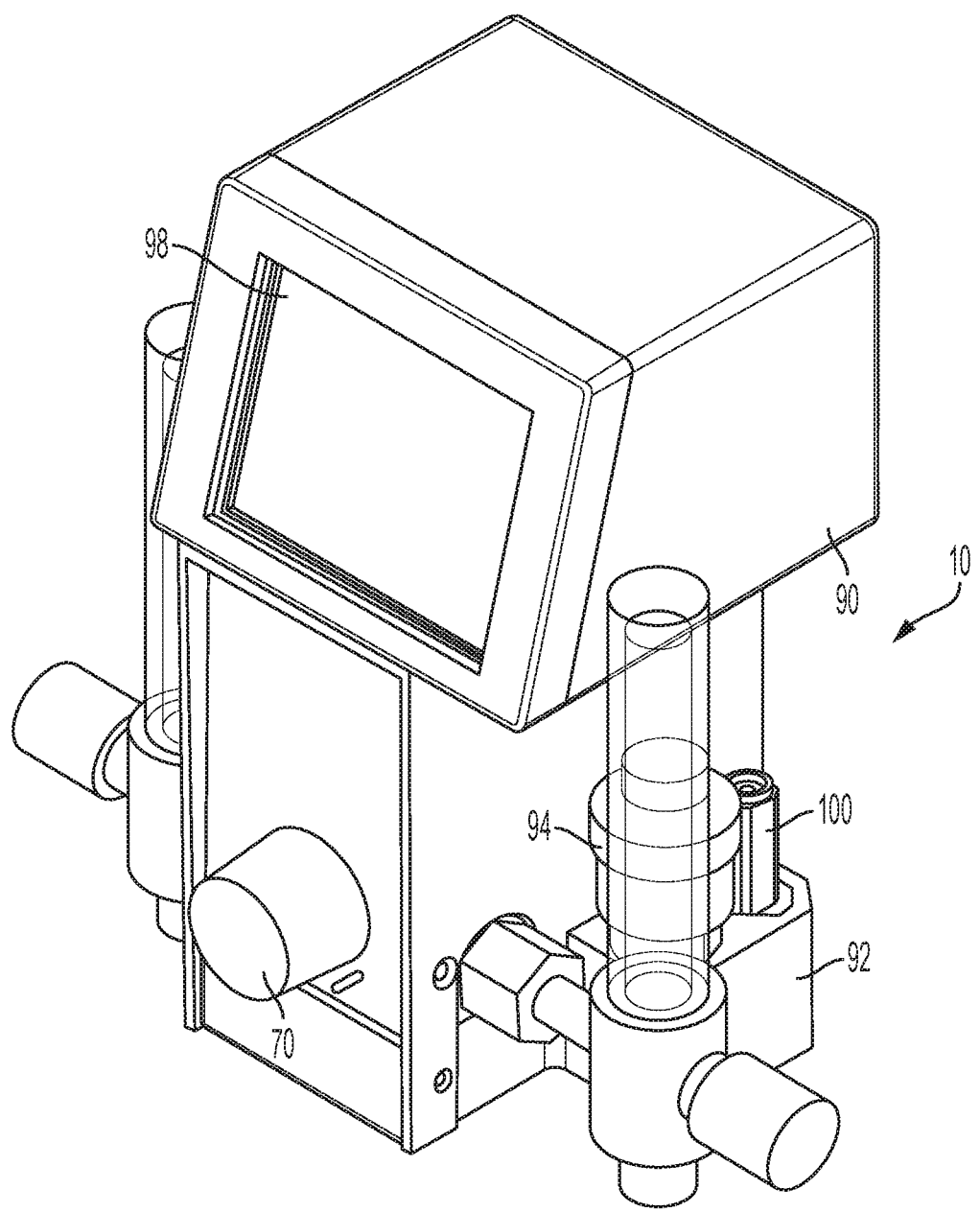
FIG. 4 is a front, top and left side isometric view of an air/oxygen blender with an associated oxygen measurement system and display, in accordance with the invention.
Figure 5:
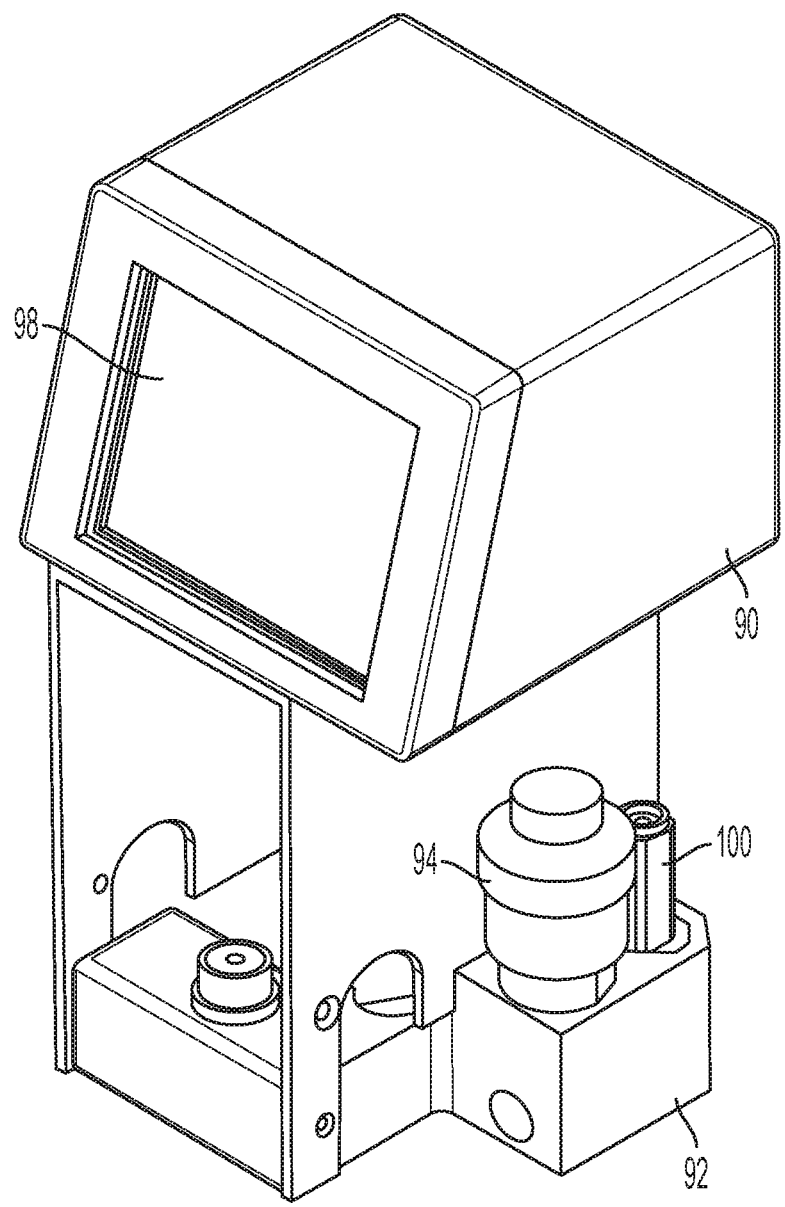
FIG. 5 is a front, top and left side isometric view of the oxygen measurement system and display of FIG. 4 with the air/oxygen blender removed.
Figure 6:
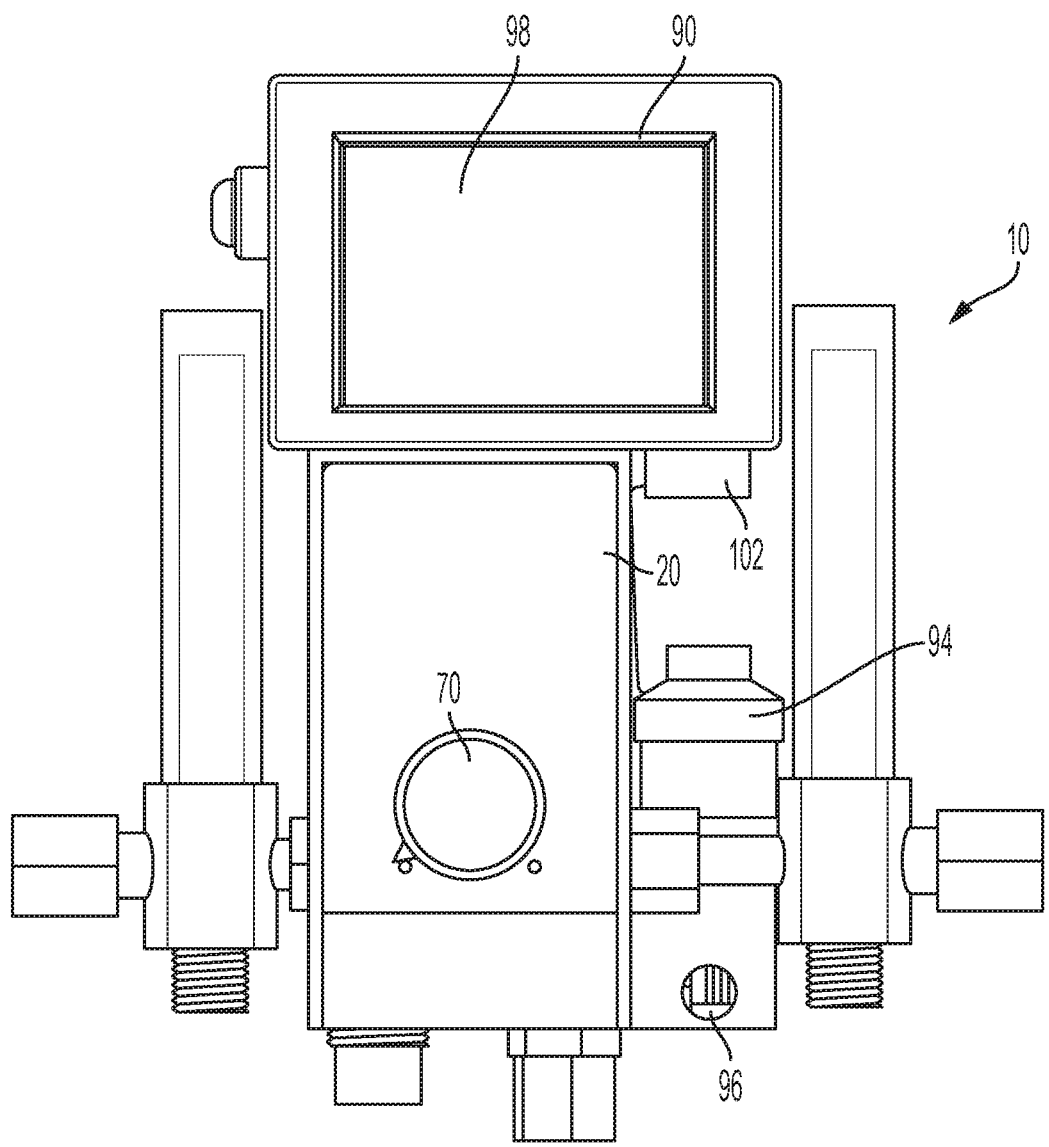
FIG. 6 is a front elevation view of the air/oxygen blender with an associated oxygen measurement system and display of FIG. 4.
Figure 7:
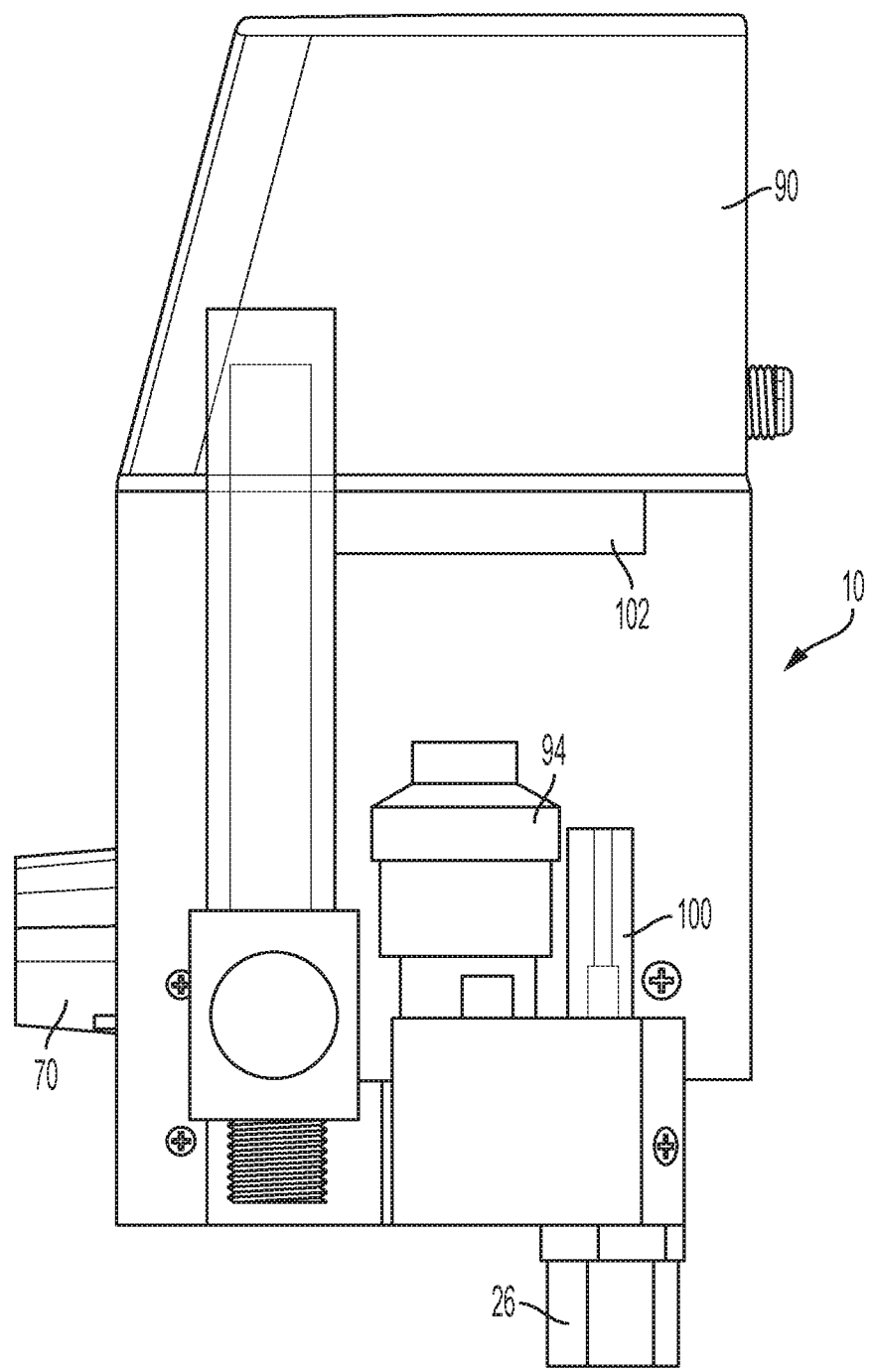
FIG. 7 is a left side elevation view of the air/oxygen blender with an associated oxygen measurement system and display of FIG. 4.
Figure 8:
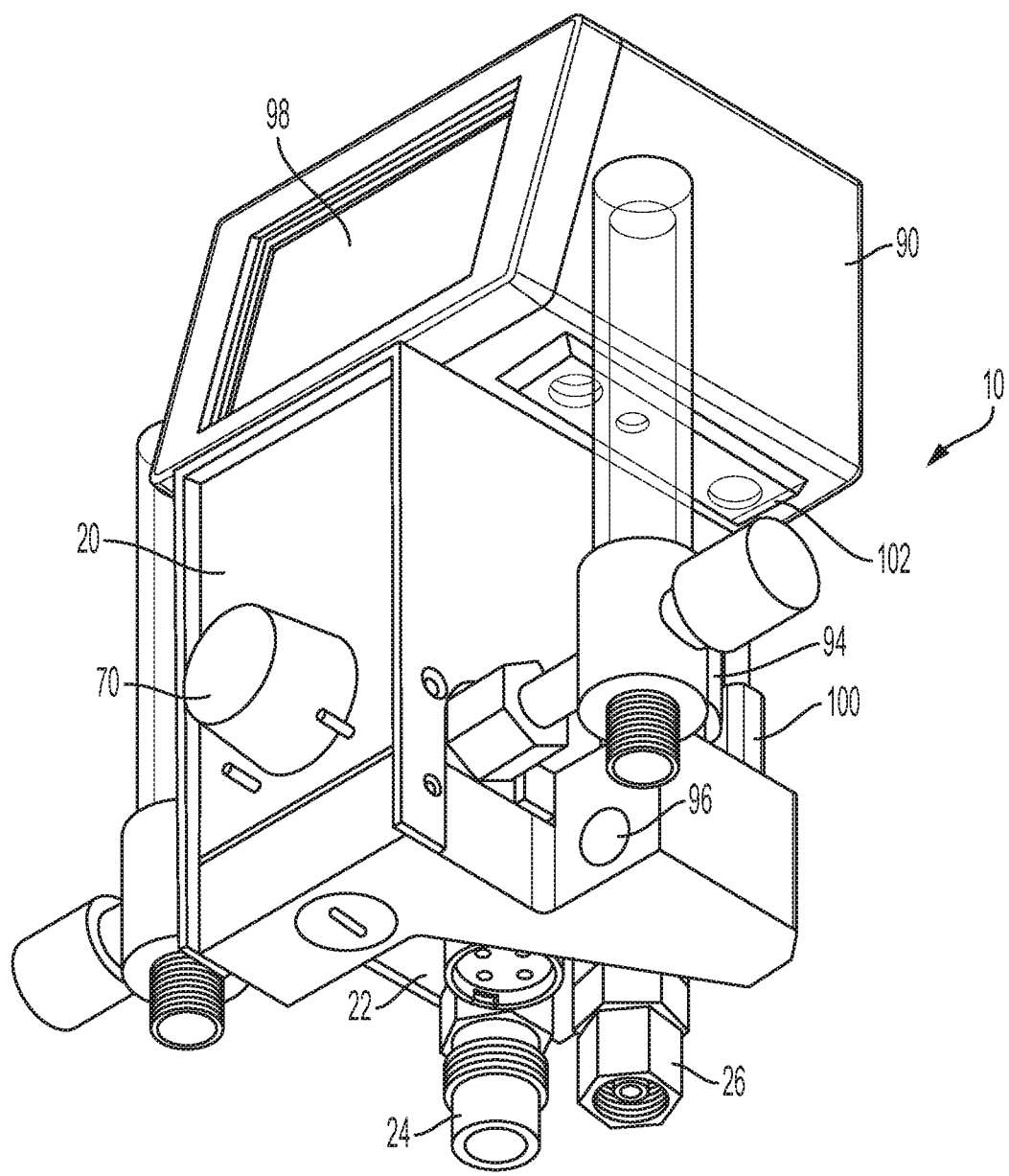
FIG. 8 is a front, bottom, and left side isometric view of the air/oxygen blender with an associated oxygen measurement system and display of FIG. 4.

With reference to FIGS. 4-13, an air/oxygen blender 10 is shown. The air/oxygen blender 10 will allow mixing of air and oxygen to provide patient ventilation air ranging from 21%-100% oxygen (0.21 to 1.0 FiO2). Air/oxygen blender 10 operates generally according to U.S. Pat. No. 3,727,627 as discussed above.

Air/oxygen blender 10 comprises a metal or plastic housing 20 having a first gas inlet 24, and a second gas inlet 26. Gas inlets 24 and 26 are D.I.S.S. fittings located on the bottom face 22 of the housing 20 and are intended for connection via tubing to a source air and a source oxygen supply supplied at a pressure of 50 psi (345 kPa) provided through a hospital distribution system or directly from tanks of compressed gas via a pressure regulator. Gas inlet 24 (air inlet) and gas inlet 26 (oxygen inlet) have particulate filters 28 and 30 provided respectively therein. Particulate filters 28 and 30 may comprise a 30 or 48 micron filter. Each of gas inlet 24 and gas inlet 26 has a duckbill check valve 32 and 34 respectively positioned in the inlet with its valve bill pointing upwards and inwards into the blender housing 20.

Air/oxygen blender 10 has two pressure balancing stages 12, 14, and a proportioning stage 16.

The first balancing stage 12 comprises a cavity 40 divided by a resilient diaphragm 42. The diaphragm 42 divides the cavity into first chamber 44 and second chamber 46. In the FIGS, first chamber 44 is an air chamber and second chamber 46 is an oxygen chamber. An inlet chamber 48 is adjacent first chamber 44, and another inlet chamber 50 is adjacent second chamber 46.

A valve spool 52 extends through and is bonded to the diaphragm 42 and extends though inlet chamber 48, first chamber 44, second chamber 46, and another inlet chamber 50.

On opposite ends or parts of valve spool 52 are valve closing structures such as ball 54 located in inlet chamber 48, and ball 56 located in inlet chamber 50. A valve seat 58 is located in an opening between inlet chamber 48 and first chamber 44, and a valve seat 60 is located in an opening between inlet chamber 50 and second chamber 46. Ball 54 seats in valve seat 58 and ball 56 seats in valve seat 60. Valve spool 52 may optionally be provided with coil spring at either end thereof which bias the spool to a center position.

Air enters from the first gas inlet 24 which is in fluid communication with the inlet chamber 48 and first chamber 44. Oxygen enters from the second gas inlet 26 which is in fluid communication with inlet chamber 50 and second chamber 46. If the air and oxygen pressures are equal the diaphragm 42 does not move and the air and oxygen will flow at the delivered pressure. If one gas is at a higher pressure, the diaphragm 42 will move towards the lower pressure chamber, simultaneously moving the valve spool 52 and a valve closing structure (e.g. ball 54 or 56) towards the valve seat 58, 60 in the higher pressure chamber, and simultaneously moving the valve closing structure (e.g. ball 54 or 56) away from the valve seat 58, 60 in the lower pressure chamber.

The gases continue to a second pressure balancing stage 14 which is the same as the first stage 12, in which a diaphragm 142 responds to any difference in source pressures and equalizes these pressures by activating a valve spool 152 to adjust air and oxygen pressures in the air and oxygen chambers.

After the pressure balancing stages 12, 14, the gases continue to a proportioning stage 16 and are mixed to the percentage dialed in on the front panel knob 70 by proportioning valve 72. The proportioning stage 16 is in fluid communication with the first gas chamber 44, and the second gas chamber 46, and one or more gas outlets. Proportioning valve 72 is a double-ended valve with valve seats on either end. One valve seat controls the passage of air and the other valve seat controls the passage of oxygen. The front panel knob is used to set the specific FiO2 blend. The knob settings range from 21% oxygen to 100% oxygen. With the front panel knob at the full counterclockwise position (21%), the double ended valve will completely close off the flow of oxygen, allowing only air to flow. By adjusting the knob to the full clockwise position (100%), the flow of air is blocked, permitting only the flow of oxygen. The blended air/oxygen delivered from the proportioning stage 16 to one or more gas outlet(s) 80, 82, 84. Each outlet has a check valve that prevents gas from passing through it unless a hose or other device is attached to it. Each outlet desirably has an on/off valve to control release of gas from the blender. Outlet 80 is a primary outlet located on one side of the housing 20. Outlet 82 is a low flow auxiliary outlet located on the lower surface of housing 20.

Air/oxygen blender 10 is provided with an associated oxygen analyzer 90. The oxygen analyzer 90 has a manifold 92 that is adapted to mount to auxiliary outlet 82 contains internal channels to deliver blended air/oxygen delivered from the proportioning stage 16 to an oxygen sensor 94 located in a sensing chamber 96. Sensing chamber 96 is in fluid communication with the proportioning stage 16 and one or more of the outlets 80, 82, 84. The oxygen sensor 94 may comprise a galvanic, partial pressure sensor having two electrodes, a membrane, and an electrolyte. Oxygen diffuses through the membrane and reacts at a gold cathode, while oxidation occurs at a lead anode, generating an electrical current and providing a voltage output. When in use, blended air/oxygen is delivered to oxygen sensor 94 in a continuous stream at a gas flow of 1 liter per minute. Oxygen analyzer 90 has an electronic display screen 98 which displays a gas oxygen percentage determined by the oxygen analyzer 90.

Air/oxygen blender 10 has an exhaust valve 100 in fluid communication with the proportioning valve 72 and the gas outlet. Exhaust valve 100 may be manually operable or electrically actuated. Exhaust valve 100 vents gas from the air/oxygen blender 10, thereby releasing pressure in the system. The release of pressure relieves any pressure imbalance between the two gas sources, thereby preventing contamination or dilution of the lower pressure source gas line with gases from the higher pressure source gas line.

Preferably, exhaust valve 100 automatically opens periodically to vent gas from the air/oxygen blender 10. Preferably, exhaust valve 100 is an electrically actuated valve, most preferably a solenoid valve, controlled by a control unit 102 which periodically actuates the exhaust valve 100 to open it. In one embodiment, the solenoid valve is a two position latching solenoid valve. A latching solenoid uses an electrical current pulse or internal permanent magnet to maintain a set position without the constant application of power. Latching solenoids (also known as bistable solenoids) have two standard positions; de-energized with the plunger fully extended and de-energized with the plunger held in position by permanent magnets.

The control unit 102 delivers 5V power to the solenoid valve in a 10-30 ms pulse to change the solenoid valve's open/closed state. Thus, the control unit 102 may activate the open state of the solenoid valve to vent gases from the air/oxygen blender 10, after which no further power is needed to maintain the open state, and then the control unit 102 will activate the closed state of the solenoid valve, after which no further power is needed to maintain the closed state.

The control unit 102 controls both the frequency of exhaust valve 100 opening and the time period of exhaust valve 100 opening. In different embodiments, different exhaust cycles may be implemented. In one embodiment, the exhaust valve 100 is activated to vent gases once every 24 hours for a 5 minute duration. Other activation frequencies may be used, such as: once every 12 hours, once every 6 hours, once every 3 hours, once every hour, and once every 30 minutes. Activation frequencies may be any appropriate period as determined by local conditions and while generally this will only need to be a once-daily occurrence, it can be more frequent, including once every one or several hours, minutes, or seconds. These different cycles will be established by the manufacturer and preprogrammed in control unit 102. The duration of exhaust valve 100 opening should be sufficient to allow dissipation of any pressure differential. An opening period of 30 seconds to 5 minutes is generally sufficient.

In some cases a higher frequency of exhaust valve opening may be desired. For example, control unit 102 may actuate exhaust valve 100 so it is (1) opened every 30 seconds for 10 seconds; (2) opened every 60 seconds for 10 seconds; (3) opened every 90 seconds for 15 seconds; (4) opened every 120 seconds for 15 seconds; or (5) opened every 180 seconds for 15 seconds.

In some embodiments, the control unit may allow a user to select one or both of the frequency of exhaust valve opening and the time period of exhaust valve opening using the control unit. However, it is preferable to have frequencies of exhaust valve opening and time period of exhaust valve opening set by the manufacturer, to minimize the possibility of a user error in these settings.

In some embodiments, the functions of control unit 102 are embedded in and accessed through the display 98 of the oxygen analyzer 90.

Exhaust valve 100 is located in any convenient location in housing 20 of air/oxygen blender 10 or in the manifold 92 of oxygen analyzer 90. In the embodiment shown in FIGS.

Figure 9:
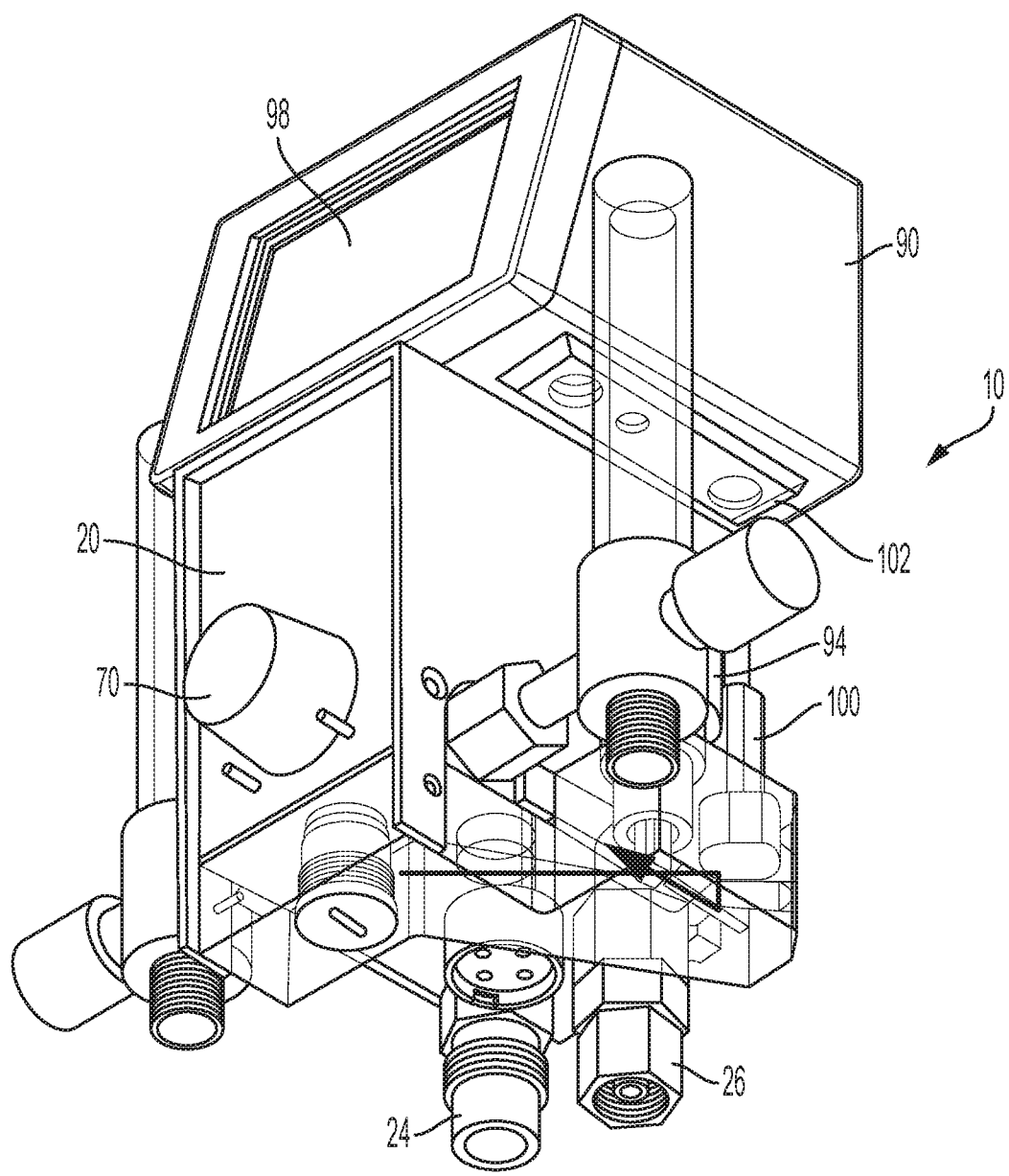
FIG. 9 is the air/oxygen blender of FIG. 8 with the oxygen analyzer manifold 92 shown with internal components shown in phantom lines to show a gas flow path through the oxygen analyzer manifold.
Figure 10:
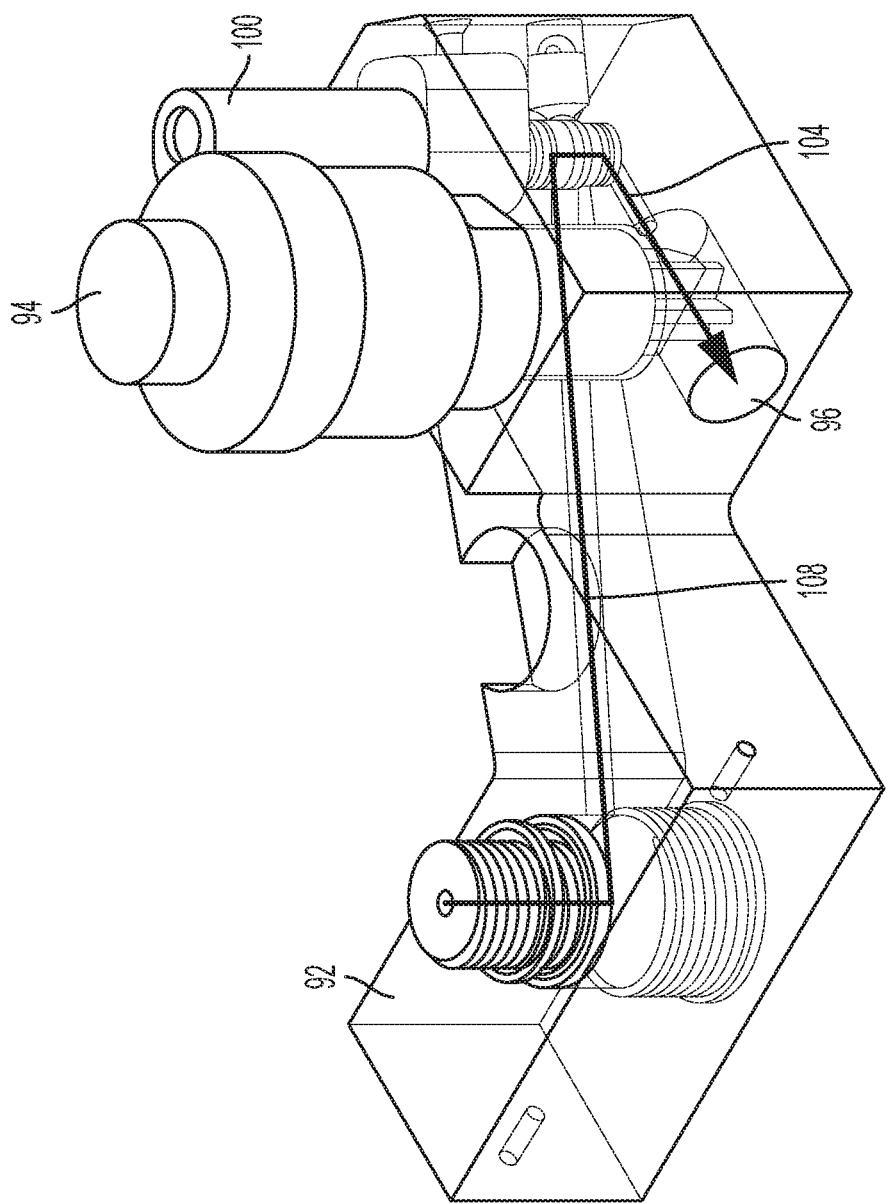
FIG. 10 is a detail view of the oxygen analyzer manifold of the air/oxygen blender of FIGS. 8 and 9 with internal components shown in phantom lines to showing a gas flow path therethrough.
Figure 11:
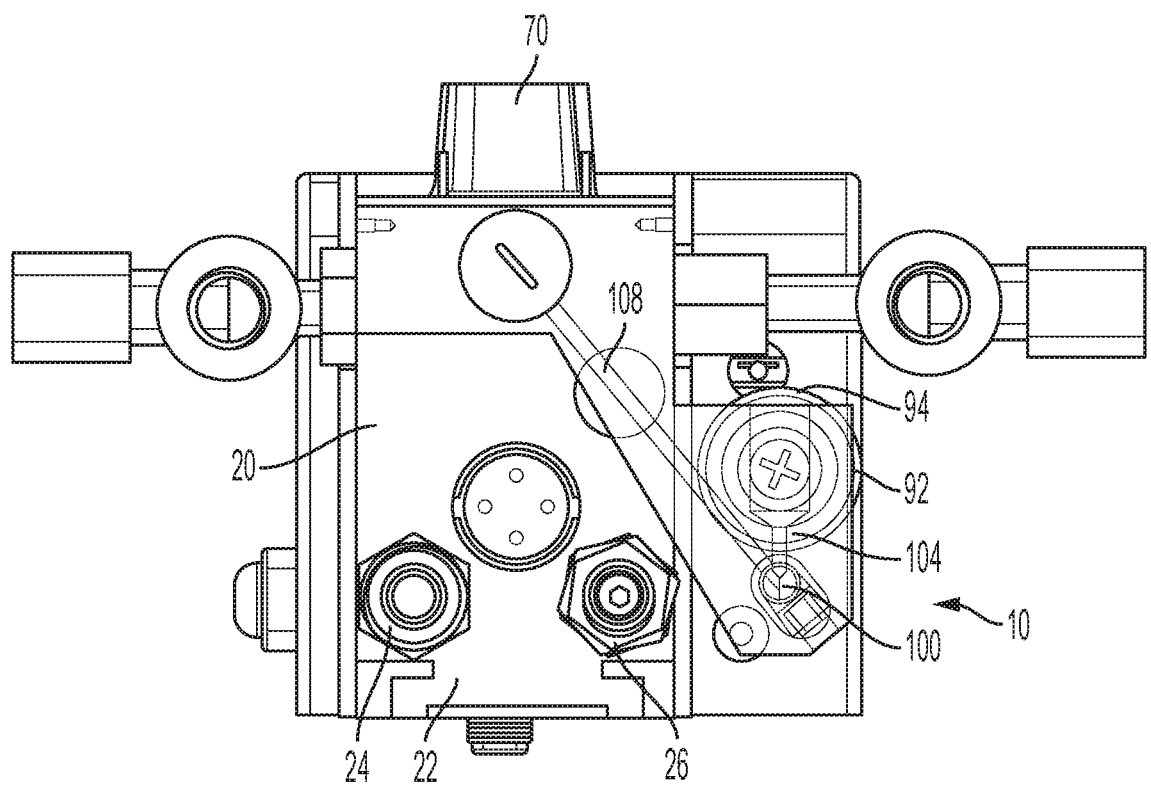
FIG. 11 is a bottom plan view of the air/oxygen blender with an associated oxygen measurement system and display of FIG. 4 with the oxygen analyzer manifold 92 shown with internal components shown in phantom lines to show a gas flow path therethrough.
Figure 12:
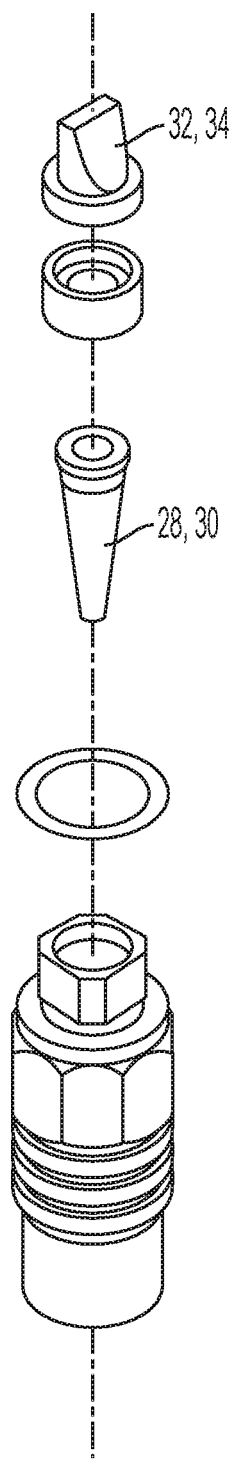
FIG. 12 is an exploded view of a gas inlet of the air/oxygen blender of FIG. 4.
Figure 13:
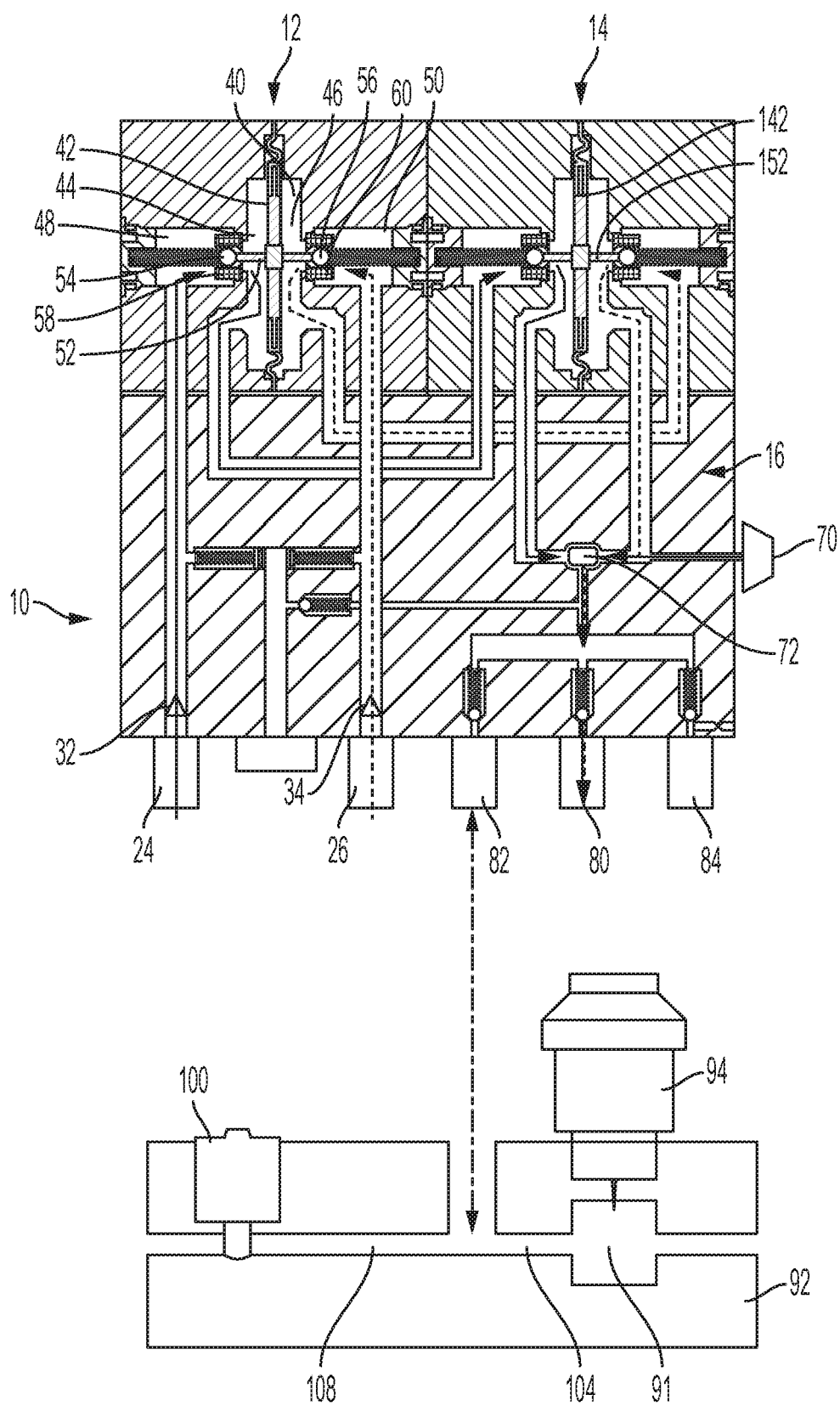
FIG. 13 is a schematic view of an air/oxygen blender with an associated oxygen measurement system and display, in accordance with the invention.

4-11, exhaust valve 100 is located in manifold 92. As seen in FIGS. 9-11, exhaust valve 100 is in fluid communication with the air oxygen blender 10 via channel 108 which extends from adjacent the auxiliary outlet 82 to exhaust valve 100. A further channel 104 connects to sensing chamber 96.

In another embodiment, as illustrated by FIG. 10, a manifold 92 may be provided separate from an air/oxygen blender and a display unit, and includes a channel 108 connecting from an inlet port to exhaust valve 100 and then via channel 104 to oxygen sensing chamber 96 and oxygen analyzer 94.

Exhaust valve 100 provides a method of prevention of contamination of a lower pressure source air or source oxygen connected to the air/oxygen blender 10. The periodic opening of the exhaust valve to vent gas from the air/oxygen blender 10 prevents pressure from building up to the point where the lower pressure source air or source oxygen is contaminated or diluted by the higher pressure source oxygen or source air, respectively.

Although the invention has been described with reference to a particular arrangement of parts, features, and the like, these are not intended to exhaust all possible arrangements or features. Indeed, many other modifications and variations will be ascertainable to those of skill in the art.

What is claimed is:

1. A gas blender, comprising:
   a housing having a first gas inlet, a second gas inlet, a proportioning valve, and a gas outlet;
   the first gas inlet being in fluid communication with a first gas chamber;
   the second gas inlet being in fluid communication with a second gas chamber;
   the proportioning valve being in fluid communication with the first gas chamber, and the second gas chamber, and the gas outlet; and
   an exhaust valve, in fluid communication with the proportioning valve and the gas outlet, the exhaust valve configured to periodically open to vent gas therefrom according to a programmed time cycle having a specified exhaust valve opening frequency and a specified exhaust valve opening time period.

2. The air/oxygen blender of claim 1, wherein the exhaust valve is an electrically actuated valve controlled by a control unit which periodically opens the exhaust valve.

3. The air/oxygen blender of claim 2, wherein the control unit controls the exhaust valve opening frequency and the exhaust valve opening time period.

4. The air/oxygen blender of claim 3, wherein the exhaust valve is a solenoid valve.

5. The air/oxygen blender of claim 1, the proportioning valve and gas outlet being in fluid communication a sensing chamber containing an oxygen sensor.

6. The air/oxygen blender of claim 5, wherein the exhaust valve is in fluid communication with the sensing chamber, and vents gases from the sensing chamber.

7. The air/oxygen blender of claim 5, further comprising an oxygen analyzer and oxygen percentage display electrically connected to the oxygen sensor.

8. The air/oxygen blender of claim 1, wherein a check valve is located between the first gas inlet and the first gas chamber, and between the second gas inlet and the second gas chamber.

9. The air/oxygen blender of claim 8, wherein the check valves are duckbill valves.

10. The air/oxygen blender of claim 1, wherein the proportioning valve is a double-ended valve with valve seats on either end operable by reciprocating motion to close or open ends of gas channels extending from the first gas chamber and the second gas chamber to thereby release either the first gas or the second gas or a mixture thereof.

11. An air/oxygen blender, comprising:
    a housing having a first gas inlet, a second gas inlet, a proportioning valve, and a gas outlet;
    the first gas inlet being in fluid communication with a first gas chamber;
    the second gas inlet being in fluid communication with a second gas chamber;
    the proportioning valve being in fluid communication with the first gas chamber, and the second gas chamber, and the gas outlet; and
    an electrically actuated exhaust valve, in open fluid communication with the proportioning valve and the gas outlet, controlled by a control unit which is configured to periodically open the exhaust valve to vent gas therefrom according to a programmed time cycle having a specified exhaust valve opening frequency and a specified exhaust valve opening time period.

12. The air/oxygen blender of claim 11, wherein the exhaust valve is a solenoid valve.

13. The air/oxygen blender of claim 11, the proportioning valve and gas outlet being in fluid communication with a sensing chamber containing an oxygen sensor, and the exhaust valve being in fluid communication with the sensing chamber, whereby the exhaust valve vents gases from the sensing chamber.

14. The air/oxygen blender of claim 13, further comprising an oxygen analyzer and oxygen percentage display electrically connected to the oxygen sensor.

15. The air/oxygen blender of claim 11, wherein a check valve is located between the first gas inlet and the first gas chamber, and between the second gas inlet and the second gas chamber.

16. The air/oxygen blender of claim 15, wherein the check valves are duckbill valves.

17. A method of prevention of contamination of a lower pressure source air or source oxygen connected to an air/oxygen blender, having a housing having a first gas inlet, a second gas inlet, a proportioning valve, and a gas outlet; and an exhaust valve, in fluid communication with the proportioning valve and the gas outlet, comprises: periodically opening the exhaust valve to vent gas therefrom according to a programmed time cycle having a specified exhaust valve opening frequency and a specified exhaust valve opening time period.

18. The method of claim 17, wherein the exhaust valve is an electrically actuated exhaust valve controlled by a control unit which periodically opens the exhaust valve to vent gas therefrom.

19. The method of claim 18, wherein the exhaust valve is a solenoid valve.

20. A gas blender, comprising:
    a housing having a first gas inlet, a second gas inlet, a proportioning valve, and a gas outlet;
    the first gas inlet being in fluid communication with a first gas chamber;
    the second gas inlet being in fluid communication with a second gas chamber;
    the Proportioning valve being in fluid communication with the first gas chamber, and the second gas chamber, and the gas outlet:
    a manifold having an inlet in open fluid communication with the gas outlet, and a sensing chamber in fluid communication with the inlet;

an oxygen sensor provided in the sensing chamber;
an oxygen analyzer electrically connected to the oxygen sensor; and
an electrically actuated exhaust valve, in open fluid communication with the inlet and the sensing chamber, controlled by a control unit which is configured to periodical open the exhaust valve to vent gas therefrom according to a programmed time cycle having a specified exhaust valve opening frequency and a specified exhaust valve opening time period.

21. The air/oxygen blender of claim 20, wherein the exhaust valve is a solenoid valve.

* * * * *